(12) United States Patent
De Groen et al.

(10) Patent No.: US 7,894,648 B2
(45) Date of Patent: Feb. 22, 2011

(54) COLONOSCOPY VIDEO PROCESSING FOR QUALITY METRICS DETERMINATION

(75) Inventors: Piet C. De Groen, Rochester, MN (US); Junghwan Oh, Arlington, TX (US); Wallapak Tavanapong, Ames, IA (US); Johnny Wong, Ames, IA (US)

(73) Assignees: Mayo Foundation for Medical Education and Research, Rochester, MN (US); Iowa State University Research Foundation, Inc., Ames, IA (US); Board of Regents, The University of Texas System, Austin, TX (US)

( * ) Notice: Subject to any disclaimer, the term of this patent is extended or adjusted under 35 U.S.C. 154(b) by 868 days.

(21) Appl. No.: 11/454,561

(22) Filed: Jun. 16, 2006

(65) Prior Publication Data
US 2006/0293558 A1 Dec. 28, 2006

Related U.S. Application Data (60) Provisional application No. 60/691,627, filed on Jun. 17, 2005, provisional application No. 60/813,144, filed on Jun. 13, 2006.

(51) Int. Cl.
*G06K 9/00* (2006.01)
*A62B 1/04* (2006.01)
*A61B 1/00* (2006.01)

(52) U.S. Cl. .......................... 382/128; 348/65; 600/101

(58) Field of Classification Search ................. 382/128; 348/65–76; 600/100–183
See application file for complete search history.

(56) References Cited

U.S. PATENT DOCUMENTS 6,709,387 B1 * 3/2004 Glukhovsky et al. ........ 600/109
7,212,230 B2 * 5/2007 Stavely .................... 348/208.1

FOREIGN PATENT DOCUMENTS

WO    WO 2006037946 A1 * 4/2006

OTHER PUBLICATIONS

Article: Poster Session, Jun. 2004, 15 pgs.*
Webpage http://www.3danaesthesia.co.uk/3D/FlexibleEndoscope-Simulator.html, Oxford's Simple Endoscope Tracker (OxSET), 8 pages, printed Feb. 16, 2010, last updated May 23, 2008.
Article: Proceedings of the 2002 IEEEE Canadian Conference on Electrical & Computer Engineering "Colour Texture Analysis Using Co-occurrence Matrices for Classification of Colon Cancer Images" J. Shuttleworth, A. Todman, R. Naguib, B. Newman, and M. Bennett pp. 1134-1139 (6 pgs).

(Continued)

*Primary Examiner*—Samir A Ahmed
*Assistant Examiner*—Fred Hu
(74) *Attorney, Agent, or Firm*—Faegre & Benson LLP (57) ABSTRACT

A computer-based method that allows automated measurement of a number of metrics that likely reflect the quality of a colonoscopic procedure. The method is based on analysis of a digitized video file created during colonoscopy, and produces information regarding insertion time, withdrawal time, images at the time of maximal intubation, the time and ratio of clear versus blurred or non-informative images, and a first estimate of effort performed by the endoscopist. As these metrics can be obtained automatically, the method allows future quality control in the day-to-day medical practice setting on a large scale. In addition, the method can be adapted to other healthcare procedures. The method may be useful to assess progress during colonoscopy training, or as part of endoscopic skills assessment evaluations.

13 Claims, 6 Drawing Sheets

OTHER PUBLICATIONS

Article: IEEE Transactions on Information Technology in Biomedicine, vol. 7, No. 3, Sep. 2003 "Computer-Aided Tumor Detection in Endoscopic Video Using Color Wavelet Features", S. Karkanis, D. K. Iakovidis, D. E. Maroulis, D. A. Karras, and M. Tzivras, pp. 141-152 (12 pgs).

Article: BioMedical Engineering OnLine, Apr. 8, 2003, "Feature extraction for the analysis of colon status from the endoscopic images", M. Tjoa and S. Krishnan, pp. 1-17.

Article: Proceedings of the 18th IEEE Symposium on Computer-Based Medical Systems (CBMS'05) "A Comparative Study of Texture Features for the Discrimination of Gastric Polyps in Endoscopic Video" D. Iakovidis, D. Maroulis, S. Karkanis, A. Brokos, (6 pgs), 2005.

Article: School of Computer Science and Information Systems "Tumor Detection in Colonoscopy using the Unsupervised k-Windows Clustering Algorithm and Neural Networks", G.D. Magoulas, V.P. Plagianokos, D.K. Tasoulis, M.N. Vrahatis, (4 pgs), In Fourth European Symposium on "Biomedical Engineering", 2004.

Article: "Using Fourier Information for the Detection of the Lumen in Endoscope images", Mr. Kwoh, Chee-Keong, Dr. Gillies, Duncan Fyfe, pp. 981-985 (5 pgs), 1994.

Article: Image Processing and its Applications, Conference Publication No. 465 @IEE 1999, "Online Extraction of Lumen Region and Boundary From Endoscopic Images Using a Quad Structure", S. Kumar, KV Asari, and D. Radhakrishnan, pp. 818-822 (5 pgs).

Article: 0-7695-2245-3/01 @2001 IEEE "A Recursive Otsu-Iris Filter Technique for High-Speed Detection of Lumen Region from Endoscopic Images", H. Tian, T. Srikanthan, and K. Vijayan Asari, pp. 182-186, (5 pgs).

* cited by examiner

← Anal Direction
→ Oral Direction

COLONOSCOPY VIDEO PROCESSING FOR QUALITY METRICS DETERMINATION

RELATED APPLICATIONS

This application claims the benefit of provisional U.S. Patent Application Ser. No. 60/691,627 titled "Colonoscopy Video Processing for Quality Metrics Determination", filed Jun. 17, 2005 and provisional U.S. Patent Application Ser. No. 60/813,144 titled "Colonoscopy Video Processing for Quality Metrics Determination" filed on Jun. 13, 2006, the entire disclosures of which are hereby incorporated herein by reference.

GOVERNMENT LICENSE RIGHTS

This invention was made with support under IIS0513809 from the National Science Foundation. The United States government may have certain rights in the invention.

TECHNICAL FIELD

The present invention relates to a system for evaluating the quality of an endoscopy video.

BACKGROUND

Advances in video technology are being incorporated into today's healthcare practices. Various types of endoscopes (a flexible tube with a tiny video camera at the tip) are used for colonoscopy, upper gastrointestinal endoscopy, enteroscopy, bronchoscopy, cystoscopy, laparoscopy, wireless capsule endoscopy, and invasive surgeries (e.g., laparoscopic surgery, arthroscopic surgery, video endoscopic neurosurgery). During an endoscopic procedure, an endoscopist advances the endoscope through the patient's anatomy. The tiny video camera generates a video signal of the interior of a human organ, which is displayed on a monitor for real-time analysis by the physician.

Colonoscopy is an important screening tool for colorectal cancer. In the US, colorectal cancer is the second leading cause of all cancer deaths behind lung cancer. As the name implies, colorectal cancers are malignant tumors that develop in the colon and rectum. The survival rate is higher if the cancer is found and treated early before metastasis to lymph nodes or other organs occurs.

The colon is a hollow, muscular tube or lumen about 6 feet long, and consists of six parts or segments: cecum with appendix, ascending colon, transverse colon, descending colon, sigmoid and rectum. Colonoscopy allows for inspection of the entire colon and provides the ability to perform a number of therapeutic operations such as biopsy and polyp removal during a single procedure. A colonoscopic procedure consists of two phases: an insertion phase and a withdrawal phase. During the insertion phase, a flexible endoscope is advanced under direct vision via the anus into the rectum and then gradually into the most proximal part of the colon or the terminal ileum. In the withdrawal phase, the endoscope is gradually withdrawn while the endoscopist moves the camera back and forth to examine suspicious regions. The purpose of the insertion phase is to reach the cecum or the terminal ileum. Careful mucosa inspection and diagnostic or therapeutic interventions such as biopsy, polyp removal, etc., are performed in the withdrawal phase.

Although colonoscopy has become the preferred screening modality for prevention of colorectal cancer, recent data suggest that there is a significant miss-rate for the detection of even large polyps and cancers. The miss-rate may be related to the quality of the video image produced during the procedure that is then reviewed by the physician or endoscopist. Current endoscopes are equipped with a single, wide-angle lens, and typically do not have camera operation function such as zoom-in, zoom-out and auto focusing. Thus, video data of colonoscopies typically have many blurry (out-of-focus) frames due to frequent shifts of camera positions while moving along the colon. Because of these limitations, a significant number of out-of-focus frames (for colonoscopy the average is about 37%, but it can be over 60% depending on the endoscopist's skill and the patient's conditions) are included in the colonoscopy video. The out-of-focus frames do not hold any useful information. Such out-of-focus or non-informative frames are usually generated for the following reasons: (1) too-close (or too-far) focus into (from) the mucosa of the colon or (2) foreign substances (i.e., stool, cleansing agent, air bubbles, etc.) covering camera lens.

In addition, non-informative frames may be caused by the endoscope camera moving too rapidly through the colon. Thus, the miss-rate, or the ability to review the endoscopy video efficiently and accurately, is related to the experience of the endoscopist in generating the endoscopy video. This is because it is the endoscopist who controls the speed of the camera's movement through the colon and when and how often the camera is moved back and forth.

In one example, current American Society for Gastrointestinal Endoscopy guidelines suggest that on average the withdrawal phase during a screening colonoscopy should last a minimum of 6-10 minutes. However, even though the withdrawal time may meet the guidelines, the quality of the colonoscopy cannot be determined if the colonoscopic procedure has a large number of out-of-focus frames in the withdrawal phase, or if a relatively low number of frames are devoted to suspicious regions. Currently, there is no measurement method to evaluate the endoscopist's skill and the quality of colonoscopic procedure.

What is needed, then, is a method of analyzing an endoscopy video to evaluate the endoscopist's skill and the quality of the endoscopy procedure.

SUMMARY

In one embodiment, the present invention is a method for evaluating the quality of an endoscopy procedure performed by inserting and withdrawing an endoscopic camera through a lumen. Digital video data containing images of an endoscopy procedure is acquired. The digital video data is analyzed to acquire information relating to movement of the camera through the lumen. From the camera movement information, at least a first quality metric relating to the endoscopy procedure is calculated.

In another embodiment, the present invention is a method for evaluating the quality of an endoscopy procedure performed by inserting and withdrawing an endoscopic camera through a lumen wherein the endoscopy procedure is recorded as digital video data containing images of the endoscopy procedure. It is determined whether an image is non-informative or informative. The informative images are analyzed to acquire information relating to movement of the camera through the lumen. From the camera movement information, at least a first quality metric relating to the endoscopy procedure is calculated.

In yet another embodiment, the present invention is a system for evaluating the quality of an endoscopy procedure performed by inserting and withdrawing an endoscopic camera through a lumen. The endoscopy procedure is recorded as digital video data containing images of the endoscopy procedure. The system includes a first means for analyzing the digital video data to acquire information relating to movement of the camera through the lumen. The system further includes a second means for calculating from the camera movement information at least a first quality metric relating to the endoscopy procedure. The system also includes a third means for assigning a satisfactory rating to the endoscopic procedure if the quality metric at least meets a predetermined threshold and assigning an unsatisfactory rating to the endoscopic procedure if the quality metric does not meet the predetermined threshold.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

The present invention is related to a computer-based method that allows automated measurement of a number of metrics that likely reflect the quality of an endoscopic procedure such as a colonoscopy. The method is based on analysis of digitized video images created during colonoscopy, and produces information regarding one or more quality metrics. The endoscopy video may be acquired digitally, or may be converted from an analog video to a digital video. In addition, the digital video file may be provided in any typical format, including, for example, as an MPEG. Each of the methods or steps described herein may be provided as part of a software program for automatically analyzing the colonoscopy and evaluating one or more quality metrics relating to the quality of the colonoscopy procedure.

Figure 1:
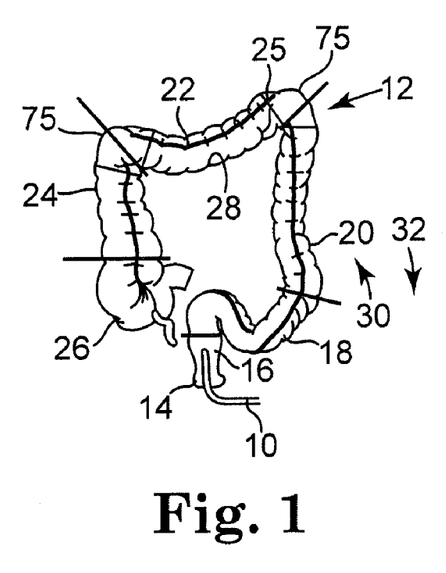
FIG. 1 shows an endoscopy camera in relation to a colon.

FIG. 1 illustrates an endoscopic camera 10 in relation to a colon 12. The camera 10 is partially inserted into the colon 12, which includes six main segments moving from the anus 14 in an oral direction, the rectum 16, the sigmoid 18, the descending colon 20, the transverse colon 22, the ascending colon 24 and the cecum 26.

There are many different quality aspects, or metrics, of a colonoscopy or other endoscopic procedure that can be evaluated to determine the endoscopist's skill and the quality of the procedure. The following are exemplary metrics in relation to a colonoscopy. However, it should be noted that the described metrics are merely examples and the invention is not so limited. Furthermore, the metrics described herein may also be applied to evaluate the quality of other endoscopic procedures in which an endoscopic camera is advanced through a tube or lumen.

One metric, hereinafter referred to as "Metric 1", measures the overall duration of the insertion phase termed the insertion time. Another metric, hereinafter referred to as "Metric 2", measures the overall duration of the withdrawal phase termed the withdrawal time. Longer insertion and withdrawal times may indicate that the endoscopist is slowly and carefully advancing the endoscope through the colon. Still another metric, hereinafter referred to as "Metric 3", measures (i) the clear withdrawal time defined as the duration of the withdrawal phase without out-of-focus frames; and (ii) the ratio of the clear withdrawal time to the overall withdrawal time defined earlier. Longer clear withdrawal times and high ratios of clear withdrawal times to overall withdrawal times may indicate that a greater number of frames are in focus and/or informative regardless of the actual overall withdrawal time.

Yet another metric, hereinafter referred to as "Metric 4", measures the number of camera motion changes and the ratio of the number of camera motion changes to the clear withdrawal time. More frequent camera motion changes, such as back and forth movements, may indicate that the endoscopist is more carefully examining the colon 12 and trying to inspect the less visible side of folds 25 in the colon 12, which are the areas where missed colorectal cancers are sometimes found.

Still another metric, hereinafter referred to as "Metric 5", measures the fraction of the clear withdrawal time that is spent for close inspections of a colon wall 28 ("wall views") and the ratio of close inspections to global inspections of the colon 12 ("lumen views"). This metric may indicate how well the colon mucosa of the colon wall 28 is inspected.

Figure 2:
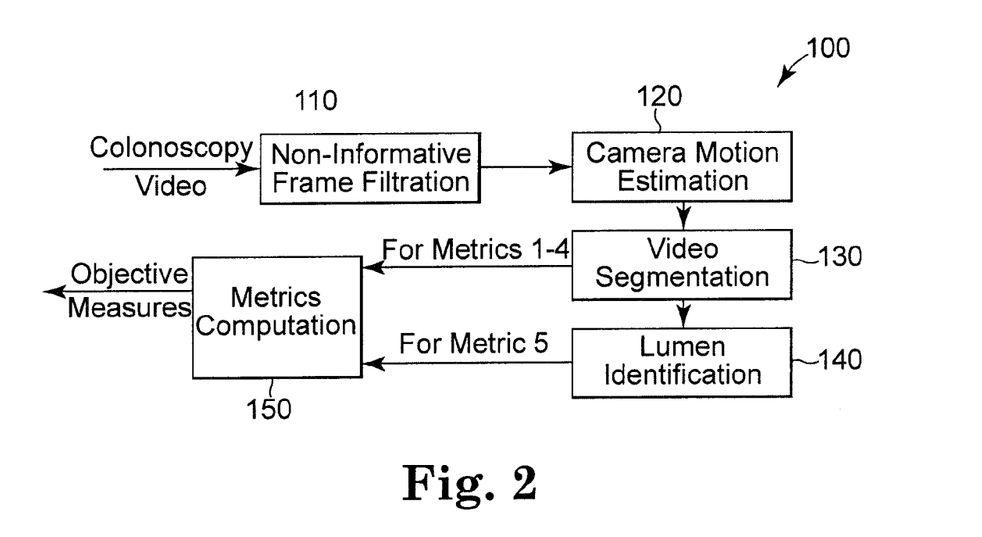
FIG. 2 shows a flowchart illustrating a process for computing quality metrics of a colonoscopy video according to one embodiment of the present invention.

To compute these and other metrics, a process 100 as shown in FIG. 2 is provided according to one embodiment of the present invention. In general, process 100 is used to analyze the images of the endoscopic procedure to acquire information relating to the movement of the camera 10 through the colon 12.

Figure 3:
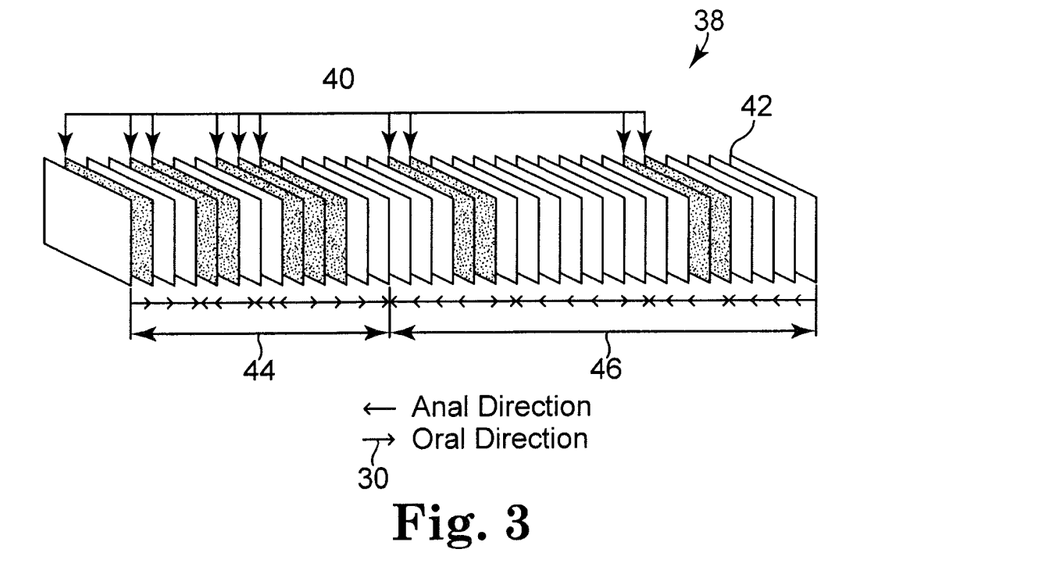
FIG. 3 shows camera motions in a colonoscopy video.

First, referring also to FIG. 3, out-of-focus or non-informative frames or images 40 from a video 38 of a colonoscopy procedure are detected and discarded in a pre-processing step (block 110 in FIG. 2). The procedure to detect and remove non-informative frames 40 from the endoscopy video 38 is referred to as "non-informative frame filtration". Informative frames or images 42 of the endoscopy video 38 are retained.

Second, the camera motions are estimated to find a boundary between an insertion phase 44 and a withdrawal phase 46 (block 120). The insertion phase 44 does not always consist of continuous forward camera motions. Likewise, the withdrawal phase 46 does not always consist of continuous backward camera motions since the endoscopist constantly moves the camera 10 back and forth to inspect the interesting regions such as polyps, cancers, the terminal ileum, the crowfoot with appendix, the ileo-cecal valve, etc., with an optimal view. Hence, either phase has an arbitrary number and combination of forward and backward camera motions while the dominant camera motions of insertion and withdrawal phases 44, 46 are forward and backward, respectively.

Third, the colonoscopy video 38 is segmented based on the camera motions such as forward and backward (block 130 in FIG. 2), which are called oral direction and anal direction, respectively, indicated by arrows 30 and 32, respectively, in FIGS. 1 and 3. A camera motion shot is defined as a sequence of consecutive frames with a single direction of camera motion. A camera motion shot can be either an oral shot which represents the camera motion from the anus 14 to the cecum 26 (forward camera motion) or an anal shot which represents the camera motion from cecum 26 to anus 14 (backward camera motion). By accumulating the values of camera motions in the oral and anal shots in an entire video, and finding a peak value, the end of the insertion phase can be located.

Fourth, lumen identification is performed to determine whether an informative frame 42 contains the colon lumen or not (block 140). A frame without the colon lumen or with the colon lumen at the periphery of the image indicates close inspection of the colon wall 28 whereas a frame containing the colon lumen, particularly when in the center of the image, indicates a more global inspection. Finally, the information regarding movement of the endoscopic camera 10 through the colon 12 garnered from the aforementioned steps (blocks 110-140) is used to compute results for one or more quality metrics (block 150).

Figure 4:
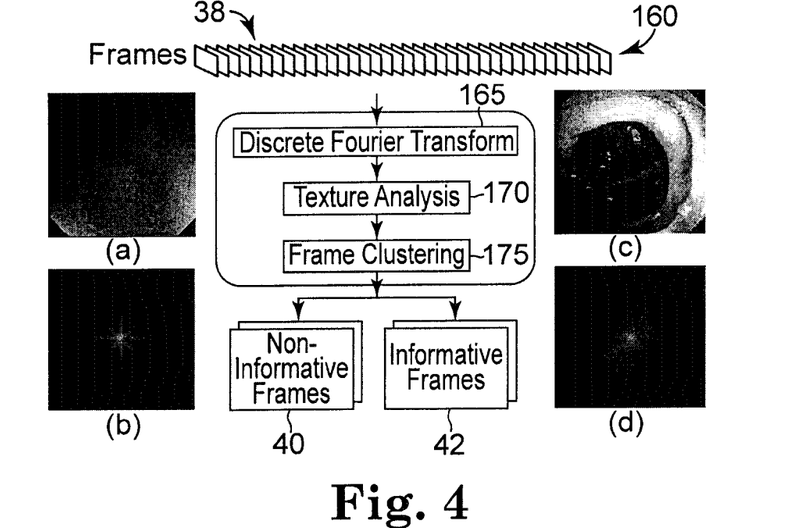
FIG. 4 shows a process for clustering-based non-informative frame filtering according to one embodiment of the present invention.

The following describes a method 160 of distinguishing non-informative frames 40 from informative frames 42 in the colonoscopy video 38 according to one embodiment of the invention. This method employs Discrete Fourier Transform (block 165), texture analysis (block 170), and frame clustering (block 175) as shown in FIG. 4. In general, use of the Fourier Transform algorithm (block 160) is based on the observation that the frequency spectrums of informative and non-informative frames exhibit different patterns. For instance, a non-informative frame (FIG. 4 (a)) has no clear object information except the four strong edges at the corners of an octagonal image running approximately at ±45° so its Fourier spectrum (FIG. 4 (b)) shows prominent components along the ±45° directions that correspond to the four corners (with the black triangles which form the only clear edges) of the image. Compared to the non-informative frame, an informative frame (FIG. 4 (c)) has a lot of clear edge information so its spectrum (FIG. 4 (d)) does not show prominent components along the ±45° directions because it has a wider range of bandwidth from low to high frequencies.

The texture analysis (block 170) is applied on the frequency spectrum image to find the difference in patterns between the informative frame 42 and the non-informative frame 40. A well-known gray-level co-occurrence matrix is used and seven texture features are extracted. The seven texture features refer generally to Entropy, Contrast, Correlation, Homogeneity, Dissimilarity, Angular Second Moment, and Energy.

The extracted features are then used to distinguish non-informative frames 40 from informative frames 42 in the colonoscopy video 38. Frame clustering (block 175) involves a two-step K-means methodology to classify frames into two groups (i.e., the informative frame group and the non-informative frame group), based on the seven texture features of these frames. In the first clustering step, the initial number of clusters is set to 3 (k=3) to cluster frames into three groups: the informative frame group, the non-informative frame group, and the in-between group. The frames classified into the in-between group from the first step are used in the next clustering step. In the second clustering step, the number of clusters is set to 2 (k=2) in order to further divide the frames in the in-between group into two groups that are the informative frame group and the non-informative frame group. Finally, all the frames are clustered into the two groups, either the informative frame or the non-informative frame groups.

Alternate means of distinguishing non-informative frames from informative frames may be employed according to other embodiments of the invention. For example, an edge detection algorithm, such as a canny edge detector algorithm, is applied to detect the presence of edges in each frame. The presence of edges in the video data would indicate that the frame is in-focus and informative, while a lack of detected edges or the presence of blurry edges would indicate that the frame is out-of-focus and non-informative.

The following describes a method of analyzing the colonoscopy video to determine the direction of motion of the camera according to one embodiment of the invention. In general, motion vectors are extracted directly from the P-frames of a colonoscopy video in MPEG format. Only the P-frames are used for two reasons. First, usually every third and fifth frame in an MPEG video is a P-frame, and thus, the temporal resolution is sufficient. Second, both the prediction direction and the temporal distance of motion vectors in B-frames do not exhibit useful patterns. After motion vectors are extracted and their outliers filtered, the video is segmented into oral and anal shots and phases.

Figure 5:
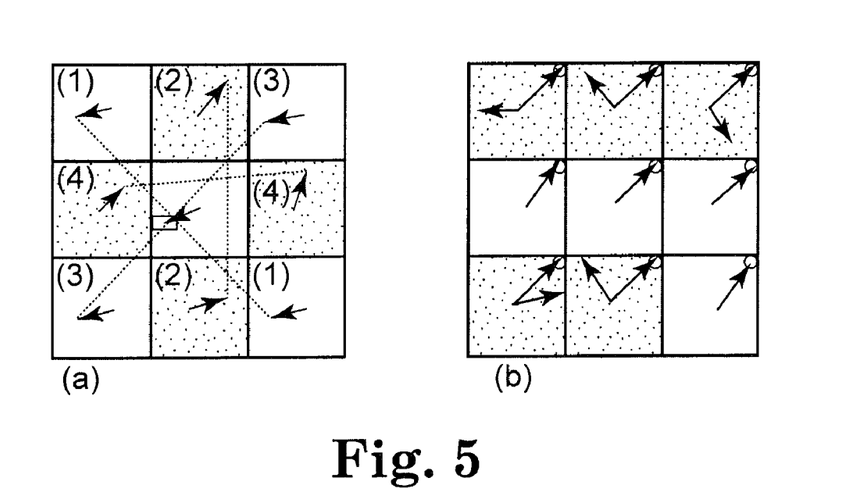
FIG. 5 shows patterns for motion vectors filtering according to one embodiment of the present invention.

To deal with motion vectors that may not be relevant, various outlier removal algorithms may be employed. Among them are heuristic methods and smoothing filters. Another method is applied on every macroblock to detect outlier motion vectors. This method includes two main steps referred to as smooth change and neighborhood. A motion vector (mv) is declared as an outlier if both the steps declare it as an outlier (see the examples in FIGS. 5(a) and (b)). Detected outlier motion vectors are then removed. The two steps for outlier detection are explained as follows.

Smooth change: The central mv is compared to each average of four pairs of opposite neighbors. If the distance between the average mv of each pair and the central mv is less than a certain threshold, it is considered a supporting pair. In FIG. 5 (a), pairs 1 and 3 are supporting pairs so the number of supporting pairs is 2. If the number of supporting pairs is below a threshold, the central mv is declared as an outlier. In one embodiment, a value 3 is used for the threshold of supporting pairs.

Neighborhood: A neighborhood motion vector supports the central mv if it lies within a tolerance angle (see FIG. 5 (b)). If the number of supporting vectors is below a threshold, then the central mv is declared as an outlier. In one embodiment, a value 4 is used for the threshold of supporting vectors.

Figure 6:
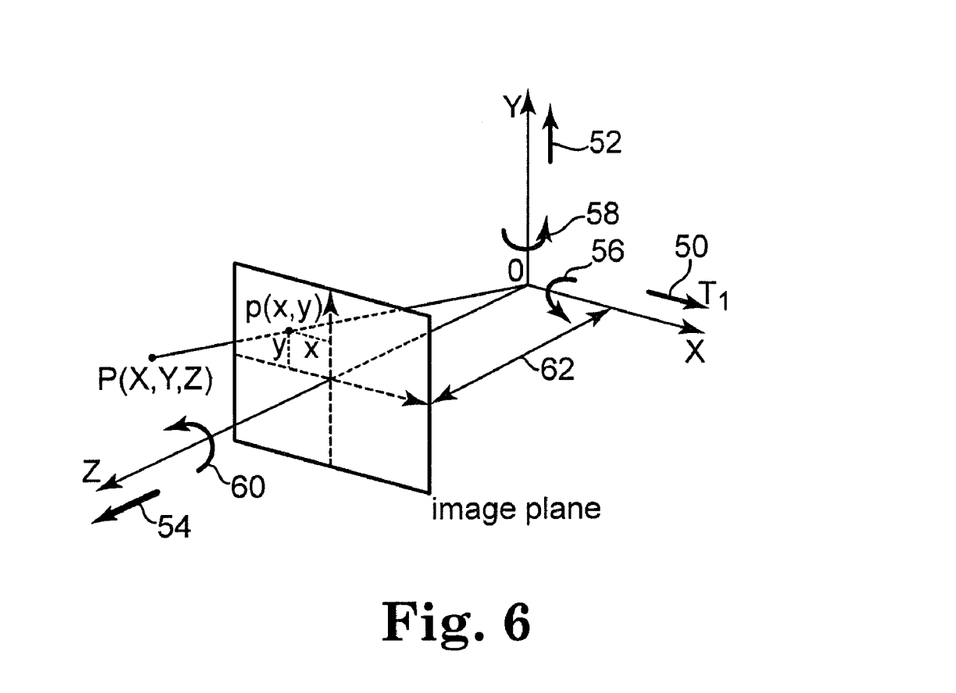
FIG. 6 shows a 3D camera motion model according to one embodiment of the present invention.

The following describes a method for estimating camera motion in a compressed MPEG video according to one embodiment of the invention. As seen in FIG. 6, seven camera motions can be defined as follows and indicated by the arrows 50-60: tracking 50 refers to translation along the X axis; booming 52 refers to translation along the Y axis; dolling 54 refers to translation along the Z axis; tilting 56 refers to rotation along the X axis; panning 58 refers to rotation along the Y axis; rolling 60 refers to rotation along the Z axis; and zooming refers to change of a focal length 62.

All seven camera motions can be expressed in an affine flow model as follows.

$$\binom{u}{v} = \quad (1)$$

$$\left[\begin{pmatrix} a_1^{zoom} & b_1^{roll} \\ -b_2^{roll} & a_2^{zoom} \end{pmatrix}\binom{x}{y} + \binom{c^{pan}}{d^{tilt}} + \frac{1}{z}\left[\begin{pmatrix} a_1^{dolly} & 0 \\ 0 & a_2^{dolly} \end{pmatrix}\binom{x}{y} + \binom{c^{track}}{d^{boom}}\right]\right]$$

where (u, v) is the motion vector of a macroblock located at position (x, y) of each frame, z is the depth of the real world, $a_1^{zoom}$, $b_1^{roll}$, $b_2^{roll}$, $a_2^{zoom}$, $c^{pan}$, $d^{tilt}$, $a_1^{dolly}$, $a_2^{dolly}$, $c^{track}$ and $d^{boom}$ are scalar coefficients concerned with camera motions. Since the endoscope 10 does not have zoom-in and zoom-out functions, $a_1^{zoom}=0$ and $a_2^{zoom}=0$. So Equation (1) can be rewritten as follows.

$$\binom{u}{v} = \begin{pmatrix} \frac{a_1^{dolly}}{z} & b_1^{roll} \\ -b_2^{roll} & \frac{a_2^{dolly}}{z} \end{pmatrix}\binom{x}{y} + \begin{pmatrix} c^{pan} + \frac{c^{track}}{z} \\ d^{tilt} + \frac{d^{boom}}{z} \end{pmatrix} \quad (2)$$

Let $$a_1 = c^{pan} + \frac{c^{track}}{z}, a_2 = \frac{a_1^{dolly}}{z}, a_3 = b_1^{roll}, a_4 = d^{tilt} + \frac{d^{boom}}{z}, a_5 = -b_2^{roll},$$

$$a_6 = \frac{a_2^{dolly}}{z}$$

Equation (2) can then be rewritten as follows $$\binom{u}{v} = \begin{pmatrix} a_2 & a_3 \\ a_5 & a_6 \end{pmatrix}\binom{x}{y} + \binom{a_1}{a_4} \quad (3)$$

Given the motion vectors, the parameter values $\{a_1, a_2, a_3, a_4, a_5, a_6\}$ can be calculated using the Least Square Fitting method. Let $\hat{u}$ and $\hat{v}$ be the estimated motion vectors, then the distance between the estimated motion vector $(\hat{u}, \hat{v})$ and the extracted motion vector (u, v) is $$Dist = \sum_x \sum_y [(\hat{u}-u)^2 - (\hat{v}-v)^2] =$$

$$\sum_x \sum_y [(\hat{u}-(a_1+a_2x+a_3y))^2 - (\hat{v}-(a_4+a_5x+a_6y))^2]$$

The parameter values are obtained when Dist is minimized and the condition for Dist to be minimized is the first derivative of Dist to 0 such that:

$$\frac{\partial Dist}{\partial a_1} = 0, \frac{\partial Dist}{\partial a_2} = 0, \frac{\partial Dist}{\partial a_3} = 0, \frac{\partial Dist}{\partial a_4} = 0, \frac{\partial Dist}{\partial a_5} = 0, \frac{\partial Dist}{\partial a_6} = 0$$

By solving the above equations, the parameter values are obtained as follows.

$$\begin{pmatrix} a_1 \\ a_2 \\ a_3 \end{pmatrix} = \begin{pmatrix} N & A & B \\ A & C & E \\ B & E & D \end{pmatrix}^{-1} \begin{pmatrix} U_1 \\ U_2 \\ U_3 \end{pmatrix} \text{ and } \begin{pmatrix} a_4 \\ a_5 \\ a_6 \end{pmatrix} = \begin{pmatrix} N & A & B \\ A & C & E \\ B & E & D \end{pmatrix}^{-1} \begin{pmatrix} V_1 \\ V_2 \\ V_3 \end{pmatrix}$$

where, $$N = \sum_x \sum_y 1, A = \sum_x \sum_y x, B = \sum_x \sum_y y, C = \sum_x \sum_y x^2,$$

$$D = \sum_x \sum_y y^2, E = \sum_x \sum_y xy, U_1 = \sum_x \sum_y u, U_2 = \sum_x \sum_y ux,$$

$$U_3 = \sum_x \sum_y uy, V_1 = \sum_x \sum_y v, V_2 = \sum_x \sum_y vx, V_3 = \sum_x \sum_y vy$$

Even though the parameter values $\{a_1, a_2, a_3, a_4, a_5, a_6\}$ are related with camera motions, reliable camera motions such as Dolling Camera Motion (DCM), Rolling Camera Motion (RCM), Horizontal Camera Motion (HCM=Panning+Tracking), and Vertical Camera Motion (V CM=Tilfing+Booming) are obtained as follows.

$$DCM = \frac{1}{2}(a_2 + a_6), HCM = a_1, RCM = \frac{1}{2}(a_3 - a_5), VCM = a_4$$

Among the four camera motions, the dolling camera motion (DCM) is primarily examined because dolling camera motion is directly related to the forward and backward camera movement. Using the dolling camera motion (DCM), the colonoscopy video is segmented into a number of shots, each of which consists of the frames with the same camera motion (oral shot or anal shot). A positive DCM value thus indicates forward movement and a negative DCM value indicates backward movement. A DCM value filtration step filters out unreliable DCM values as follows.

If there are few motion vectors (mv) between two consecutive frames, an abrupt change exists between them and the estimated camera motions are not correct. This type of error is reduced by assigning DCM=0 if the number of motion vectors is less than a certain threshold value (mv<$TH_\eta$). In one embodiment, a value 10 is used for $TH_\eta$.

The DCM tends to have an incorrect value when other camera motions such as Horizontal Camera Motion (HCM) or Vertical Camera Motion (V CM) have bigger values compared with DCM. To reduce this type of error, DCM=0 is assigned if the ratio of the magnitudes of HCM and V CM to DCM $$\left(\frac{\sqrt{HCM^2 + VCM^2}}{DCM}\right)$$

is larger than a certain threshold ($TH_\zeta$). In one embodiment, a value 1500 is used for $TH_\zeta$.

Temporal information is utilized to filter out incorrect DCMs. It is likely that any oral or anal shots have more than two frames (we are using 30 frames/second rate videos). Therefore, DCM=0 is assigned if the number of consecutive frames with the same direction is less than a certain threshold ($TH_{67}$). In one embodiment, a value 2 is used for $TH_8$.

Figure 7:
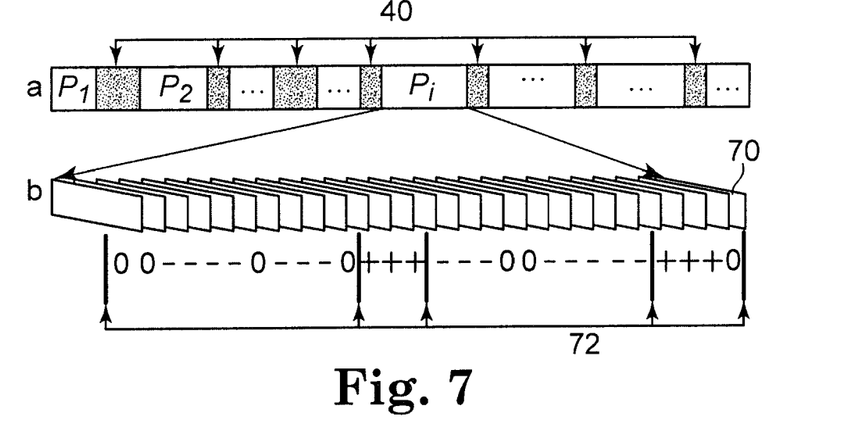
FIG. 7 shows an example of shot boundary detection according to one embodiment of the present invention.

Shot boundaries of the colonoscopy video 38 are detected in a shot boundary detection step based on camera movements. As seen in FIG. 7(a), a colonoscopy video 38 is decomposed into a number of pieces ($P_1, P_2, \ldots, P_i, \ldots$) by the non-informative frame filtration methods previously described. Each piece consists of a number of frames 70 with three different kinds of DCM values: frames with positive DCM values (+), frames with negative DCM values (−) and frames with DCM=0. Using the DCM values of frames in a piece ($P_i$), shot boundaries 72 are detected as follows. FIG. 7 (b) shows an example of the detected shot boundaries 72 using this above process.

Let $P_i$ have n numbers of frames ($F_1^i, F_2^i, \ldots, F_n^i$) and let the DCM values of these frames be $DCM_1^i, DCM_2^i, \ldots, DCM_n^i$. Two frames are considered at a time: $F_p^i$ and $F_q^i$. Initially, p=1 and q=2.

First, it is determined if the DCM value of $F_p^i$ is zero ($DCM_p^i=0$). If $DCM_p^i=0$, p and q are incremented by 1 (p=p+1 and q=q+1) until the DCM value of $F_p^i$ is not zero (i.e., forward movement or backward movement exists.)

The DCM value of $F_p^i$ ($DCM_p^i$) is compared with the DCM value of $F_q^i$ ($DCM_q^i$) until $F_1^i$ is the last frame of $P_i$ (q=n) as follows.

If $DCM_p^i \times DCM_q^i > 0$, p and q are increased by 1 (p=p+1 and q=q+1).

If $DCM_q^i = 0$, q is increased by 1 (q=q+1).

If $DCM_p^i \times DCM_1^i < 0$, a shot boundary is detected between $F_{q-1}^i$ and $F_q^i$. The two frames ($F_p^i$ and $F_q^i$) are reset such as p=q and q=q+1.

Figure 8:
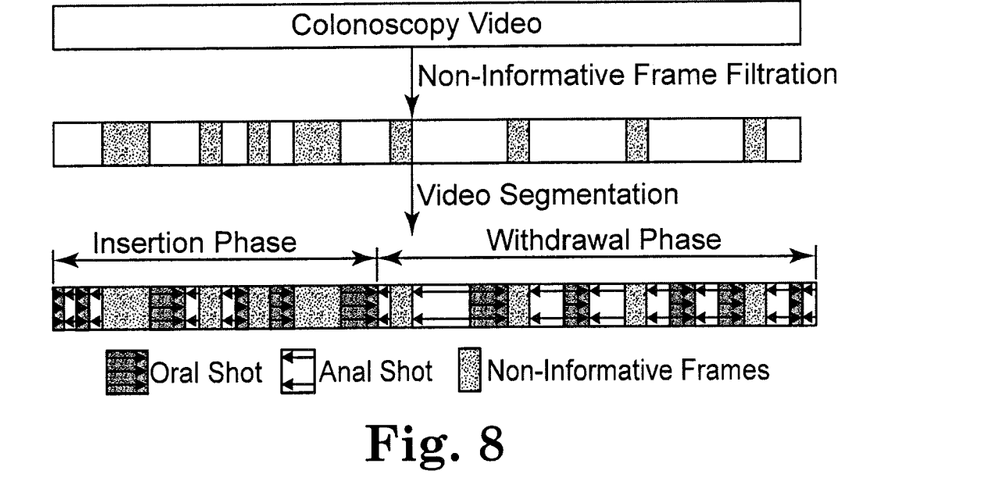
FIG. 8 shows an example of video segmentation according to one embodiment of the present invention.

A phase boundary detection step detects the boundary between the insertion phase 44 and the withdrawal phase 42 as illustrated in FIG. 3 using the accumulated DCM. FIG. 8 shows an example of video segmentation obtained using a shot and phase segmentation method according to one embodiment of the present invention. When all DCM values are added, the accumulated DCM value will increase until the end of the insertion phase because most of the frames in the insertion phase have forward movements (i.e., positive DCM values). However, the accumulated DCM value will decrease during the withdrawal phase because most of the frames in the withdrawal phase have the backward movement (i.e., negative DCM values). For this reason, the boundary frame between the insertion phase and the withdrawal phase has the highest accumulated DCM values.

Other means may be employed to segment the video. For example, pattern recognition and detection algorithms may be applied to locate "corners" 75 in the colon 12 (see FIG. 1). As the corners 75 in the colon 12 roughly separate the major portions of the colon 12, this information can be used to determine which segment of the colon 12 the camera 10 is located in for any given frame. In another example, speech recognition software may be applied to speech recorded by the endoscopist during the procedure. The endoscopist's speech is used to assign directional and segment data to each frame.

Lumen identification is used to derive the metric to evaluate mucosa inspection during the withdrawal phase. A lumen view or axial view is defined as an informative frame that contains the colon lumen whereas an informative frame without the colon lumen or with partial visualization of the lumen is called a wall view or off-axial view. A wall view occurs as a result of a close inspection of the colon wall 28 whereas the lumen view indicates a more global inspection where more than one side of the colonic wall 28 is within the field of vision. Lumen and wall views are extremes—intermediate views include part of the lumen.

Figure 9A:
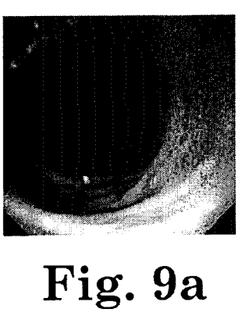
FIG. 9 shows images processed during lumen identification according to one embodiment of the present invention.
Figure 9B:
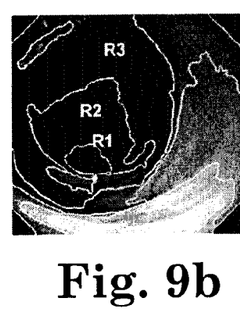
Figure 9C:
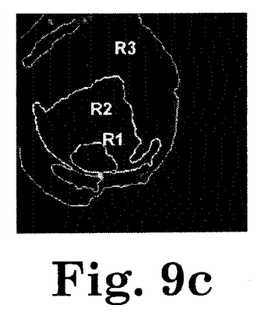

As an example, FIG. 9 (a) shows an original image with the colon lumen almost in the center. FIG. 9 (b) depicts the segmented image with the important regions, R1, R2, and R3 labeled. Region R1 is the convex region with the smallest intensity, representing the distant colon lumen. R2 is the concave region close to R1, representing a segment of the colon wall. Considering R1 and R2 together, a bilateral convex colon wall is seen. R3 is another concave region close to R2, representing another segment of the colon wall. For ease of visualization, FIG. 9 (c) is generated by masking small regions and neighboring convex regions with black pixels. FIG. 9 (c) shows only R1, R2 and R3.

In general, the colon lumen is relatively darker (R1 in FIG. 9 (b)) and there is more than one bilateral convex colon wall around the colon lumen. The relative darkness of the distant colon lumen is due to the greater scatter of light with greater distance. The intensity difference between consecutive colon walls is small. In one embodiment, an algorithm is employed to determine whether a planar region is convex or concave. Region R is considered convex if and only if for any pair of points p and q in R, the line segment connecting p and q, is completely in R; otherwise, the region is considered concave.

The image is segmented and all the regions whose size is less than a pre-defined size threshold $t_1$ are filtered out. This substantially eliminates regions that are too small and unlikely to be the distant colon lumen. $r_1$ represents the region with the lowest pixel intensity initially. If the intensity of $r_1$ is greater than another intensity threshold $t_2$ or $r_1$ is concave, this image is determined to be a wall view (no colon lumen). Otherwise, the images are analyzed as follows.

Step 1: Let $r_2$ be the closest neighboring concave region of $r_1$. Compare the intensity difference between $r_1$ and $r_2$. If the difference is larger than the intensity difference threshold $t_3$, this image is determined to be a wall view and the algorithm terminates. Otherwise, proceed to Step 2. Step 2: Let $r_1$ denote the region $r_2$ and proceed to Step 1 if this is the first time Step 2 is executed. Otherwise, the image is determined to be a lumen view and the algorithm terminates. Note that the two steps are repeated twice to check that at least two colon walls are seen together with the colon lumen before the image is determined to be a lumen view.

Alternate means of continuously grading axial frames from non-axial frames with lesser or greater angles of view away from the longitudinal axis of the colon may be employed according to the other embodiments of the invention. For example, an algorithm is used to detect the region of the lowest pixel intensity (in general the most distant lumen) in a frame, and a vector is drawn from the center of the frame to the center of the region of the lowest pixel density. The length of the vector is proportional to the degree of off-axis view, and the direction of the vector is related to the location of the distant lumen in relation to the center of the image.

The information to calculate the quality metrics as previously described is obtained from preceding steps for analyzing the digital video data to acquire information regarding camera movement.

Metric 1, which measures the overall duration of the insertion phase, the insertion time (IT), can be measured as follows:

$$IT = \frac{NF^0}{\text{Frame Extraction Rate}}$$

where $NF^0$ represents the number of frames in the insertion phase.

Metric 2, which measures the overall duration of the withdrawal phase, the withdrawal time (WT), is calculated as follows:

$$WT = \frac{NF^1}{FrameExtractionRate}$$

where $NF^1$ represents the number of frames in the withdrawal phase.

Metric 3, which measures (i) the clear withdrawal time defined as the duration of the withdrawal phase without out-of-focus frames; and (ii) the ratio of the clear withdrawal time to the overall withdrawal time, is obtained by adding up the duration of all oral and anal shots in the withdrawal phase, and is computed as follows:

$$CWT = \frac{NIF^1}{FrameExtractionRate}, \quad WT = \frac{CWT}{WT}$$

where $NIF^1$ represents the number of informative frames in the withdrawal phase.

Metric 4, which measures the number of camera motion changes and the ratio of the number of camera motion changes to the clear withdrawal time, is obtained as follows. Back and forth camera movements can be estimated by measuring the number of camera motion changes in the withdrawal phase (NCMC), and the ratio of the number of camera motion changes to the clear withdrawal time (RCMC) as follows:

$$NCMC = NS^1, \quad RCMC = \frac{NCMC}{CWT}$$

where NS1 represents the number of oral and anal shots in the withdrawal phase.

Metric 5, which measures the fraction of the clear withdrawal time that is spent for close inspections of a colon wall 28 and the ratio of close inspections to global inspections of the colon 12, is obtained as follows. The number of wall views (NWV 1) and the number of lumen views (NLV 1) are measured during the withdrawal phase. The close-global inspection ratio and close inspection fraction are computed as follows:

$$\text{close} - \text{global inspection ratio} = \frac{NWV^1}{NLV^1}$$

$$\text{close inspection fraction} = \frac{NWV^1}{NIF^1}$$

The close-global inspection ratio helps to see whether the endoscopist has produced an appropriate ratio of both close inspections and global inspections in which the colon lumen is seen. The close inspection fraction reveals the fraction of the clear withdrawal time spent on examining the colon walls very closely.

Using the non-informative frame filtration and video segmentation techniques previously described to acquire information relating to the movement of the camera 10 through the colon 12, the following information is obtained from three representative colonoscopy videos labeled 200, 210 and 217 (Table 5). Column "NF" represents the number of frames, column "NIF" represents the number of informative frames and column "NS" represents the number of shots. The superscript of each column represents the phase ID (i.e., 0 for the insertion phase and 1 for the withdrawal phase).

TABLE 1

Information of Colonoscopy Videos

| | Insertion Phase | | | Withdrawal Phase | | |
|---|---|---|---|---|---|---|
| ID | $NF^0$ | $NIF^0$ | $NS^0$ | $NF^1$ | $NIF^1$ | $NS^1$ |
| 200 | 23534 | 5615 | 423 | 12900 | 7427 | 147 |
| 210 | 8771 | 2281 | 296 | 18888 | 12836 | 262 |
| 217 | 13694 | 3004 | 258 | 19320 | 11748 | 186 |

The quality metrics generated from automatic analysis of videos in Table 1 are shown in Table 2.

Metric 1: In one embodiment, insertion time is computed as $IT=NF^0/30$ because 30 frames are extracted per second. The results are summarized in the second column of Table 2. The colonoscopy 210 has a short insertion time (about 5 minutes) and colonoscopy video 200 has a long insertion time (about 13 minutes). Many foreign substances such as stools were found during the insertion phase of colonoscopy video 200 so it was more difficult for the endoscopist to reach the proximal end of the colon. Therefore, it has a bigger IT value.

Metric 2: The withdrawal time (WT) is computed as $WT=NF^1/30$. All three colonoscopy procedures comply with established guidelines. The details are listed in the third column of Table 2.

Metric 3: The clear withdrawal time is measured as $CWT=NIF^1/30$ and the ratio of the clear withdrawal time to the withdrawal time as (CWR=CWT/WT). Even though colonoscopy video 200 may satisfy guidelines for withdrawal time, the actual mucosal inspection time of colonoscopy video 200 is lower than those of other colonoscopy videos because it has a CWT of about 4 minutes and the lowest ratio of the clear withdrawal time to the entire withdrawal time (CWR=0.576). The withdrawal time of colonoscopy video 217 is a little bit longer than that of colonoscopy video 210, but the clear withdrawal time of colonoscopy video 210 is longer than that of colonoscopy video 217. The details are found in the forth and fifth columns of Table 2.

Metric 4: The number of the camera motion changes (NCMC) is measured as ($NCMC=NS^1$) and the ratio of the number of the camera motion changes (RCMC) to the clear withdrawal time is measured as (RCMC=NCMC/CWT). There are some regions in colonoscopy video 210 that the endoscopist apparently can not see well so the endoscopist frequently moves a camera back and forth to examine these regions in order to get the best possible view. Colonoscopy video 210 has bigger values of NCMC and RCMC than the other videos so the colonoscopy video 210 may represent a colon that is different from the other two colons, and may contain more angulations or haustrae which require more efforts in order to achieve optimal mucosal inspection. The details are presented in the sixth and seventh columns of Table 2.

TABLE 2

Automated Quality Metrics

| ID | IT (min:sec) | WT (min:sec) | CWT (min:sec) | CWR | NCMC | RCMC |
|---|---|---|---|---|---|---|
| 200 | 13:4 | 7:10 | 4:7 | 0.576 | 147 | 0.594 |
| 210 | 4:52 | 10:29 | 7:7 | 0.680 | 262 | 0.612 |
| 217 | 7:36 | 10:44 | 6:31 | 0.608 | 186 | 0.475 |

Metric 5: For evaluation of this metric, 1 frame was extracted per second from the withdrawal phase of a colonoscopy video 220. Table 3 shows the ground-truth in column "Reference" and the results from video analysis as described herein. The ground truth indicates that close inspections are about 33% of global inspections and that wall inspections are about 25% of the colon mucosa inspections. The metrics according to the present invention are close to those of the ground-truth. The parameters for video analysis includes a size threshold of 1500 pixels (about 1% of the total number of pixels), an intensity threshold of 128, and an intensity difference threshold of 175.

TABLE 3

Metric 5 for mucosa inspection of video 220

| Metrics | Reference | Software |
|---|---|---|
| # informative frames (NIF1) | 549 | 549 |
| # wallviews (NWV 1) | 135 | 117 |
| # lumen views (NLV 1) | 414 | 432 |
| Close-global inspection ratio | 0.33 | 0.27 |
| Close inspection fraction | 0.25 | 0.21 |

Based on the results of quality metrics analysis as described herein, the quality of the endoscopy video can be determined. For example, the endoscopy video may be assigned a rating indicating good quality if one or more or a combination of the aforementioned metrics meets predetermined standards. Conversely, the endoscopy video may be assigned a rating indicating poor quality if one or more or a combination of the aforementioned metrics fails to at least meet a predetermined threshold.

The video analysis and computations described herein may be written into a software program for analysis of digital videos. The metrics described herein can thus be obtained automatically, such that a method of evaluating an endoscopic procedure in accordance with various embodiments of the present invention allows quality control in a day-to-day medical practice setting on a large scale. The systems and methods described herein may be useful to assess progress during colonoscopy training, or as part of other endoscopic skills assessment evaluations. In addition, the method can be adapted to other healthcare procedures.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A system for evaluating objective quality of a colonoscopy procedure performed with an endoscope having a camera, comprising:
an input for receiving information representative of the colonoscopy procedure, including colonoscopy images of the inner lining of a human colon, including colon mucosa;
a processor coupled to the input to process the images of the colon, generate data representative of the colonoscopy procedure, and compute a set of quality metrics representative of the quality of the colonoscopy procedure as a function of the colonoscopy procedure data, the set of quality metrics including: a) withdrawal time, wherein the withdrawal time is representative of a duration of a withdrawal phase during which the endoscope is withdrawn from the colon, b) clear withdrawal time, wherein the clear withdrawal time is representative of the withdrawal time less a duration of non-informative images, c) number of camera motion direction changes, d) ratio of the number of camera motion direction changes to clear withdrawal time, and e) close-global inspection ratio, wherein the close-global inspection ratio is representative of a ratio of colon wall view images to colon lumen view images; and
an output coupled to the processor for outputting the computed quality metrics.

2. The system of claim 1 wherein:
the processor further generates a rating of the colonoscopy procedure as a function of the set of quality metrics; and
the colonoscopy procedure rating is outputted at the output.

3. The system of claim 1 wherein:
the information representative of the colonoscopy procedure received at the input further includes audio information representative of the location of the endoscope in the colon; and
the processor computes at least some of the quality metrics as a function of the audio information.

4. The system of claim 1 wherein the processor processes the images to identify informative images and non-informative images, and computes one or more of the quality metrics including the clear withdrawal time metric as a function of the informative and non-informative images.

5. The system of claim 1 wherein the processor processes the images to identify a boundary between an endoscope insertion phase and an endoscope withdrawal phase, and computes one or more of the quality metrics as a function of the boundary.

6. The system of claim 1 wherein the processor processes the colonoscopy images to identify segment information representative of oral direction images and anal direction images, and computes one or more of the quality metrics as a function of the segment information.

7. The system of claim 1 wherein:
the processor processes the images to compute informative image information representative of informative images and non-informative images, and computes one or more of the quality metrics as a function of the informative image information;
the processor processes the images to compute boundary information representative of the boundary between an endoscope insertion phase and an endoscope withdrawal phase, and computes one or more of the quality metrics as a function of the boundary information; and
the processor processes the images to compute segment information representative of oral direction images and anal direction images, and computes one or more of the quality metrics as a function of the segment information; and
the processor processes the colonoscopy images to compute lumen information representative of lumen view images and wall view images, and computes one or more of the quality metrics as a function of the lumen information.

8. The system of claim 7 wherein:
the information representative of the colonoscopy procedure includes audio information; and
the processor processes the colonoscopy audio information to compute one or more of the quality metrics.

9. The system of claim 7 wherein:
the processor further generates a rating of the colonoscopy procedure as a function of the set of quality metrics; and
the colonoscopy procedure rating is outputted at the output.

10. A system for evaluating objective quality of a colonoscopy procedure performed with an endoscope having a camera, comprising:
an input for receiving information representative of the colonoscopy procedure, including colonoscopy images of the inner lining of a human colon, including colon mucosa;
a processor coupled to the input to process the colonoscopy procedure information, including:
a non-informative frame filtration section to compute informative image information representative of informative images and non-informative images;
a camera motion estimation section to compute boundary information representative of a boundary between an endoscope insertion phase and an endoscope withdrawal phase;
an image segmentation section to compute segment information representative of oral direction images and anal direction images;
a lumen identification section to compute lumen information representative of lumen view images and wall view images; and
a metrics computation section to compute a plurality of quality metrics representative of the quality of the colonoscopy procedure as a function of the informative video information, the boundary information, the segment information, and the lumen information including: a) withdrawal time, wherein the withdrawal time is representative of a duration of the endoscope withdrawal phase, b) clear withdrawal time, wherein the clear withdrawal time is representative of the withdrawal time less a duration of non-informative images, c) number of camera motion direction changes, d) ratio of the number of camera motion direction changes to clear withdrawal time, and e) close-global inspection ratio, wherein the close-global inspection ratio is representative of a ratio of wall view images to lumen view images; and
an output coupled to the processor for outputting the computed quality metrics.

11. The system of claim 10 wherein the input receives audio information representative of the colonoscopy procedure and the metrics computation section computes one or more of the quality metrics as a function of the audio information.

12. The system of claim 11 wherein:
the processor further generates a rating of the colonoscopy procedure as a function of the plurality of quality metrics; and
the colonoscopy procedure rating is outputted at the output.

13. The system of claim 1 wherein the processor processes the colonoscopy images to compute lumen information representative of lumen view images and wall view images, and computes one or more of the quality metrics as a function of the lumen information.

* * * * *